United States Patent [19]

Suarez

[11] Patent Number: 5,972,592
[45] Date of Patent: Oct. 26, 1999

[54] INCREASING REPRODUCTIVE EFFICIENCY OF BULL SEMEN USING FUCOSE OR A COMPOUND WITH A FUCOSE MOIETY

[75] Inventor: Susan S. Suarez, Ithaca, N.Y.

[73] Assignee: Cornell Research Foundation, Inc., Ithaca, N.Y.

[21] Appl. No.: 08/998,934

[22] Filed: Dec. 29, 1997

[51] Int. Cl.⁶ .................................................. A01N 1/02
[52] U.S. Cl. .............................. 435/2; 424/93.7; 424/561
[58] Field of Search ................................ 435/2; 424/93.7, 424/561

[56] References Cited

U.S. PATENT DOCUMENTS

| | | | |
|---|---|---|---|
| 3,185,623 | 5/1965 | Smith et al. | 435/2 |
| 3,347,745 | 10/1967 | Rinfret et al. | 62/67 |
| 3,444,039 | 5/1969 | Rajamannan | 435/2 |
| 3,766,008 | 10/1973 | Macomber | 435/2 |
| 3,940,943 | 3/1976 | Sikes et al. | 62/64 |
| 3,973,003 | 8/1976 | Colas | 424/561 |
| 4,329,337 | 5/1982 | Sexton | 424/561 |
| 5,045,446 | 9/1991 | Goodrich, Jr. | 435/2 |
| 5,153,004 | 10/1992 | Goodrich, Jr. | 424/533 |
| 5,554,527 | 9/1996 | Fickenscher | 435/372 |
| 5,580,714 | 12/1996 | Polovira | 435/2 |
| 5,601,972 | 2/1997 | Meryman | 435/2 |

OTHER PUBLICATIONS

Lefebvre, R., et al., Biology of Reproduction 53, 1066–1074 (1995).
Lefebvre, R., et al., Biology of Reproduction 56, 1198–1204 (May 1997).
Suarez, S. S., et al., Biology of Reproduction 56, 447–453 (Feb. 1997).
Suarez, S. S., et al., Biol. Reprod. 56 (Suppl. 1), p. 121 Abstract 154 (Aug. 1997).
GlycoTech Technical Catalog, Techniques in Glycobiology, vol. 1, p. 63 (undated).
Foote, R. H., et al., J. Dairy Sci. 80, 3072–3076 (1997).

*Primary Examiner*—Sandra E. Saucier

[57] ABSTRACT

Inclusion of fucose or fucose-containing bull sperm monovalent binding oligosaccharide in semen extender increases the reproductive efficiency of bull semen extended therewith, for artificial insemination of cows by increasing non-return rates for normal concentrations of sperm and providing acceptable non-return rates at sperm concentrations lower than 5 million motile sperm per insemination.

21 Claims, 2 Drawing Sheets

INCREASING REPRODUCTIVE EFFICIENCY OF BULL SEMEN USING FUCOSE OR A COMPOUND WITH A FUCOSE MOIETY

The invention described herein was made at least in part in the course of work under grant numbers 93-37203-9644 and 9702913 from the United States Department of Agriculture. The United States Government has certain rights in the invention.

TECHNICAL FIELD

This invention is directed to a bull semen extender composition, to extended bull semen composition and to a method of increasing the reproductive efficiency of bull semen for artificial insemination of cows.

BACKGROUND OF THE INVENTION

Most dairy cattle are bred by artificial insemination. Frozen semen is used by top producers to inseminate 95% of cows and 89% of heifers. Semen is extended (diluted) and frozen until thawed for use for insemination. A single ejaculate from a good bull can be used to inseminate as many as 1,000 cows. Presently, sperm dilution is normally considered to be limited to a concentration of not less than 5 million motile sperm for a ½ ml insemination (not less than 10 million motile sperm per milliliter). This dilution provides a "non-return" rate of 70% if conditions are optimal. The non-return rate refers to the failure of cows to return to the estrous state and therefore is directly correlated with incidence of pregnancy. Typically, 10 to 30 million bull sperm are inseminated in a volume of 0.5 ml to obtain a non-return rate of 50 to about 75%. So even if artificial insemination is used to significantly increase the reproductive efficiency of valuable bulls, millions of sperm are still needed for insemination. It is of interest to the dairy industry to be able to improve the non-return rate or reduce the number of sperm required per insemination.

We turn now to some technical background from which the invention was conceived. It has been discovered that for cows sperm become trapped in the oviduct just beyond the entrance to the oviduct by sticking (binding) to the inner surface of the wall of the oviduct (referred to hereinafter sometimes as "oviductal epithelium"). This results in formation of a sperm reservoir. As the time of ovulation approaches, sperm are released from the reservoir to fertilize the egg. Capacitation is considered to change the sperm to cause said release. It has been found that the molecules on the oviductal epithelium provide certain sugar moieties which bind to molecules on sperm and that this causes the binding of sperm to oviductal epithelium and formation of a sperm reservoir thereon. Binding of sperm to oviductal epithelium and release therefrom may serve the functions of reducing or preventing polyspermic fertilization and of prolonging the life and fertility of sperm (i.e., maintaining sperm fertilizing capacity). Thus, the binding of sperm to oviductal epithelium to form a sperm reservoir is considered a beneficial occurrence and important to fertilization. Research is and has been carried out on how sperm transport is regulated by oviductal epithelium. Fucose has been detected on the oviductal epithelial surface and sperm binding is reduced when fucose is enzymatically removed from the epithelial surface, indicating that fucose is what sperm bind to when they enter the oviduct. Furthermore, it has been discovered that the application of fucose, polymerized fucose, and fucose linked in certain linkages in oligosaccharide, inhibits the binding of the sperm to oviductal epithelium presumably by competitive inhibition of binding, i.e., by binding to sperm so fucose in oviductal epithelium cannot bind to sperm.

SUMMARY OF THE INVENTION

The invention relies on a parallel and similar but different occurrence in the uterus to what has been found to occur in the oviduct. It is known that some sperm stick (bind) to uterine wall. Other sperm are phagocytized by white blood cells. Some sperm are lost through the cervix. Therefore, in the cow, while millions of sperm are placed in the uterus by artificial insemination, only thousands reach the oviduct. Sperm sticking to uterine epithelium that are not released and whose passage toward the oviduct is retarded causes reduction in the number of sperm entering the oviduct. Thus, unlike in the case of sperm binding to oviduct wall, sperm binding to uterine wall is considered counterproductive to fertilization.

The same or very nearly the same fucose-containing molecules are present in uterine epithelium as are present in oviductal epithelium, although in lower numbers.

It is conceived by the inventor herein that similar to what is the case for oviductal epithelium, fucose in uterine epithelium binds to sperm and competitive inhibition of such by including a fucose-containing bull sperm monovalent binding compound in semen extender to bind to sperm to thereby inhibit its binding to fucose in uterine epithelium (because carbohydrate binding glycoprotein, i.e., lectin, in the sperm is already bound to fucose of the extender) will cause more sperm to reach the oviduct so as to provide increased potential for pregnancy and that this occurrence does not detract from the beneficial effects of binding of sperm to oviduct epithelium to the extent of negating the attainment of increase in reproductive efficiency (because the extender does not reach the oviduct and therefore the fucose-containing compounds reaching the oviduct do so in an amount less than that which would negate the attainment of the increase in reproductive efficiency).

In one embodiment of the invention herein there is provided a bull semen extender composition comprising fucose-containing bull sperm monovalent binding compound in a reproductive efficiency increasing effective amount.

In a second embodiment of the invention herein there is provided an extended bull semen composition which comprises bull semen and a bull semen extender composition comprising fucose-containing bull sperm monovalent binding compound in a reproductive efficiency increasing effective amount.

In a third embodiment of the invention herein there is provided a method of increasing the reproductive efficiency of bull semen for artificial insemination of cows comprising diluting it with bull semen extender composition comprising fucose-containing bull sperm monovalent binding compound in a reproductive efficiency increasing effective amount.

The application of the embodiments herein causes an increase in reproductive efficiency.

The term "bull" as used herein refers to a *Bos taurus* bovine bull.

The term "semen" as used herein means semen with sperm present therein.

The term "monovalent binding" is used herein to mean the ability to bind to only one sperm.

In the context of the invention, the phrase "increase in reproductive efficiency" means greater non-return rates (increased pregnancy rates) or the obtainment of acceptable non-return rates even though less sperm than the presently considered lower limit amount of 5 million motile sperm per insemination are employed.

Normally, 0.5 ml of extended bull semen composition is used for an insemination, and this amount of extended bull semen composition may be referred to as a breeding unit or as an inseminate.

DETAILED DESCRIPTION

Figure 1:
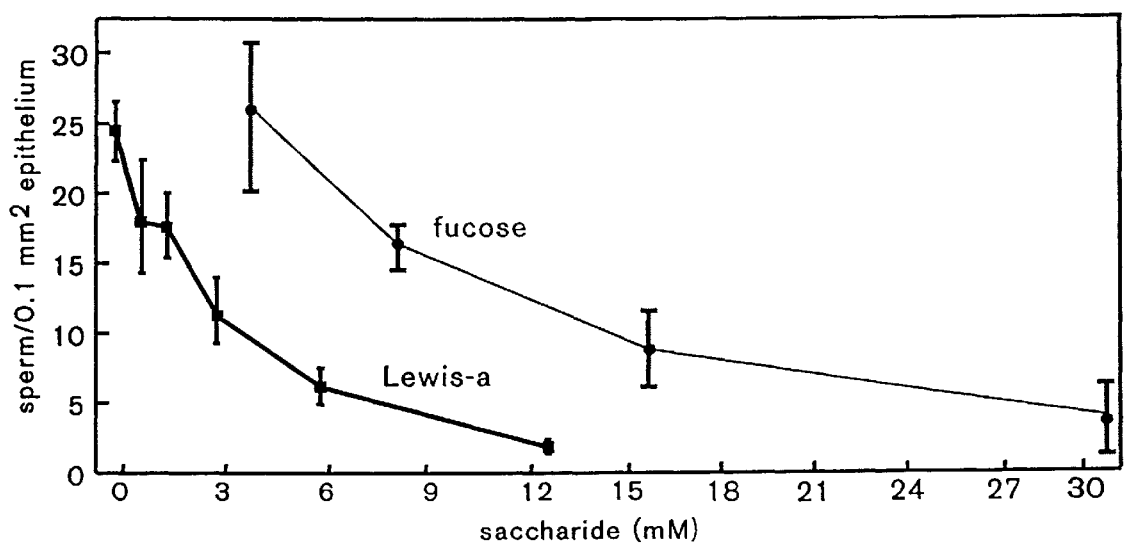
FIG. 1 depicts curves showing dose response effects of fucose and Lewis-a on sperm binding. The upper curve depicts results of an experiment of Reference Example B and shows dose response effects of fucose on sperm binding. The lower curve depicts results of the fourth set of experiments of Reference Example A and shows dose response effects of Lewis-a on sperm binding.

We turn now to the embodiment of the invention providing a bull semen extender composition comprising fucose-containing bull sperm monovalent-binding -compound in a reproductive efficiency increasing effective amount.

We turn first to the fucose-containing bull sperm monovalent binding compound component of the bull semen extender composition of the invention. The limitation on the fucose-containing compounds to monovalent binding is important because binding of a fucose-containing compound to more than one sperm can cause agglutination of sperm and agglutinated sperm do not swim normally and cannot swim from the uterus to the oviduct to cause pregnancy. A preferred method for determining fucose-containing bull sperm binding compounds comprises testing a fucose-containing compound for inhibiting binding of sperm to oviductal epithelium by the test method described in Reference Example A hereinafter. Alternatively, fucose-containing bull sperm binding compounds can be determined by testing a fucose-containing compound for binding to sperm by labeling a putative compound with a visual marker such as fluorescein, incubating the labeled compound with sperm, and determining whether the visual marker becomes associated with sperm (e.g., by using fluorescence microscopy in the case where fluorescein is utilized as the visual marker). Testing for monovalency can be carried out by determining whether a compound which is determined to bind to sperm causes agglutination of living sperm with results of no agglutination indicating monovalency. Testing for agglutination is readily carried out by adding test substance to 100 $\mu$l aliquots of two million motile sperm per milliliter of sperm medium to provide concentrations of 0 $\mu$M, 1 $\mu$M, 10 $\mu$M, 100 $\mu$M, 1 mM, 10 mM of test substance therein, incubating the mixtures at 39° C. for 15 minutes, placing 10 microliter drops on slides and examining the drops under a microscope for agglutination. Fucose-containing bull sperm monovalent binding compounds include, for example, fucose itself and fucose-containing bull sperm monovalent binding oligosaccharides. A suitable fucose-containing bull sperm monovalent binding oligosaccharide is oligosaccharide containing fucose in an $\alpha$1–4 linkage to N-acetylglucosamine, e.g., Lewis-a which is ($\alpha$-L-fucose[1–4]-[$\beta$-D-galactose-(1–3)]-D-N-acetylglucosamine) and is described in Nilsson, K. G. I., et al., Journal of Carbohydrate Chemistry 16 (4–5), 459–477 (1997). Other suitable fucose-containing bull sperm binding oligosaccharides are, for example, the disaccharide fucose (1–4)-N-acetylglucosamine or that compound where N-acetylglucosamine is also bound to other sugars which do not provide additional binding sites, and 3'-sialyl-Lewis-a. Polymeric fucose which provides more than one binding site, e.g., fucoidan, is not suitable for use herein because it is not a monovalent binding compound and while it causes the beneficial effect of competitively inhibiting binding of sperm to uterine epithelium, it causes the unacceptable negative effect of sperm agglutination.

The reproductive efficiency increasing effective amount for the fucose-containing bull sperm monovalent binding compound is that concentration in the bull semen extender composition which binds to at least 30% of sperm added to the composition. Normally, said concentration ranges from 0.5 mM to 100 mM or if the molecular weight of the compound is not readily determinable from 0.5 mg/ml to 10 mg/ml. Fucose is preferably present in the extender composition at a concentration ranging from 7.5 mM to 75 mM, very preferably from 12 mM to 50 mM. Fucose-containing bull sperm monovalent binding oligosaccharide is preferably present in the extender composition at a concentration ranging from 1 mM to 20 mM, very preferably from 5 mM to 15 mM. It is noted that cow's milk normally contains fucose-containing compound in very small amount which is considered to be less than a reproduction efficiency increasing effective amount even if the fucose-containing compound is a bull sperm binding compound if present in greater concentration. The concentrations of fucose-containing sperm monovalent binding compound used are relatively high compared to the number of sperm binding moieties in uterine epithelium which are likely to be multivalent. This is because the monovalent binding to sperm of the fucose-containing compound in the extender is of relatively low affinity and a high concentration of binding compound in extender is important to outcompete the uterine binding moieties in respect to binding.

The bull semen extender composition of the present invention can be prepared by reformulating any of the presently used bull semen extender compositions to contain fucose-containing bull sperm monovalent binding compound in a reproduction efficiency increasing effective amount.

The bull semen extender compositions now used normally have an osmolality ranging from 280–320 mOsm. This is because if the osmolality of the extender composition is too high, the high-osmotic pressure associated with such can destroy the lectin on the sperm which binds to oviductal epithelium, whereas if the osmolality of the extender composition is too low, water can rush into the sperm and destroy them. The reformulation mentioned above preferably preserves the osmolality range mentioned above so that a bull semen extender composition of the present invention preferably has an osmolality ranging from 280–320 mOsm.

Two principal kinds of bull semen extenders are now used. One of these is milk (cow's milk) based. The other is egg yolk based.

A milk based extender might contain, for example, 90–95% by volume milk and 5–10% by volume cryoprotectant (e.g., glycerol). Skim milk has been used in place of whole milk by some.

An egg yolk based extender might contain, for example, from 20 to 50% by volume egg yolk, from 5–10% by volume cryoprotectant (e.g., glycerol) and from 70 to 45% by volume buffer solution. One kind of buffer solution used consists of sodium citrate in the form of sodium citrate dihydrate in water, e.g., 2.9 g sodium citrate dihydrate per 100 ml double-distilled water. Another kind of buffer solution can contain 24.2 g Tris buffer, 15 g citric acid monohydrate and 12.5 g glucose (as a metabolic substrate for sperm) in 1,000 ml double-distilled water.

If the extender composition is to be used directly, i.e., without freezing, then the cryoprotectant preferably is omitted.

Both milk based and egg yolk based extenders normally contain antibiotics, for example, penicillin, streptomycin, and polymyxin B, with gentamicin being an alternative for penicillin and/or streptomycin.

Examples of preparation of bull semen extenders now used are as follows:

A milk based extender now used is made as follows:

Homogenized whole milk is heated to 95° C. for 10 minutes, cooled and filtered. Then antibiotics are added. The composition is then divided into two fractions which are of equal volume after 14% by volume glycerol is added to one of the fractions. The fractions are used in combination to provide extended semen compositions.

Examples of preparations now used of egg yolk based extenders are as follows:

In one case: Fresh eggs are washed with water and wiped with 70% ethanol. The shells are dried and then opened with a sterile knife. Egg yolks are separated from the whites aseptically. The egg yolk is mixed in a range of 1:1 to 1:5 by volume with sodium citrate (2.9 g sodium citrate dihydrate in 100 ml double-distilled water). If the composition is to be frozen (either before or after sperm are added thereto), glycerol is added to 7% by volume.

In another case: A solution is made up by adding 24.2 g Tris buffer, 15 g citric acid monohydrate and 12.5 g glucose to 1,000 ml double-distilled water. Egg yolk obtained as described in the above paragraph is added to the solution to make up 20% of the total volume. Then the antibiotics, penicillin, streptomycin, and polymyxin B are added. If the composition is to be frozen (either before or after sperm are added thereto), glycerol is added to 7% by volume.

For conversion of presently used bull semen extenders to bull semen extender composition of the invention herein, fucose can be added to a presently used extender by making up a solution of 300 mM fucose in sterile, double-distilled water and adding it to the presently used bull semen extenders at 1:10 (10% by volume) and fucose-containing oligosaccharide as described above can be added to a presently used extender by making up a solution of 100 mM fucose-containing oligosaccharide and adding it to the presently used bull semen extenders at 1:10 (10% by volume). The osmolality is preferably adjusted to range from 280–320 mOsm if a composition is otherwise obtained with too high an osmolality by excluding sufficient milk or egg yolk to reduce the osmolality to be within the aforementioned range.

We turn now to the embodiment of the invention providing an extended bull semen composition which contains bull semen and a bull semen extender composition comprising fucose-containing bull sperm monovalent binding compound in a reproductive efficiency effective amount. The extended bull semen composition can be prepared, for example, simply by adding bull semen to the bull semen extender composition of the above-described embodiment or by adding the semen to a fraction of the extender composition and then combining this admixture with remaining fraction of the extender composition or by adding the semen to a portion of components or amounts thereof of the extender composition and then adding the remainder of components or amounts thereof of the extender composition. Bull semen is normally included in the extender composition in an amount to provide a concentration of bull sperm in the formed extended bull semen composition, ranging from $1\times10^6$ motile sperm/ml to $100\times10^6$ motile sperm/ml, i.e., in an amount to provide $0.5\times10^6$ motile sperm to $50\times10^6$ motile sperm per one-half milliliter inseminate. The invention herein allows the obtaining of acceptable or good non-return rates even though the bull sperm is present in the extended bull semen composition in an amount less than the unofficially recognized lower limit of 10 million motile sperm per ml (5 million motile sperm per one-half milliliter inseminate) or the customary lower limit of 20 million motile sperm per ml (10 million motile sperm per one-half milliliter inseminate). Therefore, an important application of the invention herein is an extended bull semen composition comprising a concentration of bull sperm less than $5\times10^6$ motile sperm per one-half ml inseminate, for example, an extended bull semen composition comprising bull sperm at a concentration ranging from $2\times10^6$ to $4\times10^6$ motile sperm per one-half milliliter inseminate, or comprising a concentration of bull sperm less than $20\times10^6$ motile sperm per ml, for example, an extended bull semen composition comprising bull sperm ranging from $10\times10^6$ motile sperm/ml to $15\times10^6$ motile sperm/ml, that is, from $5\times10^6$ to $7.5\times10^6$ motile sperm per one-half milliliter inseminate. The addition of the sperm to the extender to provide the extended bull semen composition herein is readily carried out by admixing as described below in reference to the third embodiment herein. The extended semen is preferably packaged in 0.5-ml straws (one straw being used for each insemination), sealed and frozen within 4 hours after glycerol addition. The cooling rate is preferably approximately −15° C./min from +5 to −100° C. After freezing, the straws can be transferred to liquid nitrogen for storage. For use, the straw, i.e., breeding unit, is thawed by immersing the straw in 30–37° C. water for one-half to one minute, and insemination is carried out by expelling the extended sperm from the straw into a cow's uterus using a plunger device as is conventional.

We turn now the third embodiment herein, that is to the embodiment providing a method of increasing the reproductive efficiency of bull semen for artificial insemination of cows comprising diluting bull semen with bull semen extender composition comprising fucose-containing bull sperm monovalent binding compound in a reproductive efficiency increasing effective amount. The bull semen extender composition for this embodiment is that which is the first embodiment herein. The amount of bull semen which is diluted in this embodiment is that set forth in the description of the second embodiment herein. The dilution, i.e., addition of semen to extender composition, is readily carried out by any of the methods of semen dilution conventionally employed. A preferred method of dilution in the context of the invention herein comprises forming an admixture of semen and extender composition as follows: The extender without cryoprotectant and fucose-containing compound is divided into two fractions which are of equal volume after glycerol cryoprotectant and solution of fucose-containing compound are added to the second fraction. The first fraction is placed in a water bath at 35° C. and tubes of collected semen are placed in the same water bath. One part of semen is admixed with three to four parts of first fraction by addition of first fraction to the semen and this admixture is cooled from 35° C. to 50° C. over about 2.5 hours. The cooled partially extended semen is then further extended by addition of first fraction at 50° C. to one-half the final volume. The second fraction is then added dropwise to provide the final volume.

The extended bull semen composition of the invention herein is readily employed to artificially inseminate cows (including heifers) by any of those methods conventionally employed for artificially inseminating cows, for example, the method described at pages 905–906 of Veterinary Obstetrics and Genital Diseases (Theriogenology)* by Steven J. Roberts, published by the author Woodstock, Vt. 05091 (1986), distributed by David and Charles Inc., North Pomfret, Vt. 05053, which are incorporated herein by reference.

As used herein, the term "cow" includes heifers unless the context indicates otherwise.

As indicated above, the invention herein increases the reproductive efficiency of bull semen. In one aspect, this means using conventional concentrations of bull semen and obtaining higher than normal non-return rates, e.g., non-return rates over 80%. In another aspect, this means using concentrations of bull semen providing sperm concentrations less than the presently considered minimum of 5 million motile sperm/one-half ml inseminate, e.g., those concentrations less than 10 million motile sperm/ml described above, and obtaining non-return rates greater than 70% or 75% or 78% or even 80%.

The invention is illustrated by the following examples and is described in conjunction with the following background and reference examples.

EXAMPLE I

Extended semen composition is made up as follows:

Homogenized whole milk is heated to 95° C. for 10 minutes, cooled to 24° C. and filtered. The treated whole milk is divided into two fractions the second of which contains 34% by volume less than the first.

To 66 ml of second fraction is added 14 ml glycerol and 20 ml fucose solution. Fucose solution is made up by dissolving 19.69 g of L-fucose in double-distilled water to make up 430 ml. The 100 ml resulting from combination of 66 ml of second fraction, 14 ml glycerol and 20 ml fucose solution is denoted fraction B.

A 50 ml portion of the first fraction is denoted fraction A.

Fraction A is placed in a water bath at 35° C. and tubes of collected semen are placed in the same water bath.

Semen (7 ml) is extended with 21 ml fraction A by dropwise addition of fraction A to the semen and the admixture is cooled in a waterjacket to 5° C. over a period of 3 hours.

The resulting admixture is further extended with an additional 22 ml fraction A at 5° C. by dropwise addition.

Then an equal volume of fraction B is added dropwise.

The final concentration of fucose is 27.9 mM and the concentration of motile sperm in the composition is $30 \times 10^6$ per ml.

The extended semen is packaged in 0.5-ml straws so that each straw contains $15 \times 16^6$ motile sperm and is frozen in the straws within 4 hours after the final admixture is formed. The cooling rate is approximately –15° C./min and cooling is from +5° C. to –100° C. The resulting filled straws at –100° C. are transferred to liquid nitrogen for storage.

Field trials were carried out using straws containing fucose in a concentration of about 30 mM and sperm in an amount of $15 \times 10^6$ motile sperm per straw in 50% of cases and using straws made the same but containing an equal volume of milk in place of the fucose solution for the other 50% of cases.

To make up the straws, semen from each of three bulls was divided into two equal parts, and half was used for fucose-containing straws and half was used for control straws.

The extended semen reformulated to include fucose was found not to be detrimentally affected by the fucose in respect to sperm motility after freezing and thawing.

A total of 401 cows were inseminated by technicians who were unaware of different compositions being used or that fucose was included in some compositions. The non-return rates for first service (i.e., first insemination) are reported in the Table 1 below:

TABLE 1

| Treatment | # 1st services | # non-returns | % non-returns |
|---|---|---|---|
| Control | 163 | 30 | 79.8% |
| Fucose-added | 238 | 96 | 82.4% |

The difference obtained is significant ($p \leq 0.05$).

Similar results of increased non-return rates are obtained when the extender is prepared by including fucose in egg yolk/glycerol extender buffered to pH of about 7.4 with citrate or Tris buffer, as compared to the egg yolk/glycerol/citrate or Tris buffered extender without fucose.

EXAMPLE II

A test is carried out as set forth in Example I except that bull sperm is present in the fucose-containing extended bull semen composition at a concentration of $10 \times 10^6$ motile sperm per straw and a non-return rate of 75% is obtained.

A test is carried out as set forth in Example I except that bull sperm is present in the fucose-containing extended bull semen composition at a concentration of $5 \times 10^6$ motile sperm per straw and a non-return rate of 75% is obtained.

A test is carried out as set forth in Example I above except that bull sperm is present at a concentration of $2 \times 10^6$ motile sperm per straw and a non-return rate of 75% is obtained.

EXAMPLE III

Semen was packaged in 0.5 ml straws together with extender consisting of those listed below so that each straw contained $20 \times 10^6$ sperm and the packaged semen was cooled to 5° C. and then at a rate of –15° C./minute to –100° C. and then was stored in liquid nitrogen.

Extenders were made up as follows:

An egg yolk/citrate extender was made up by mixing egg yolk 1:5 by volume with sodium citrate (2.9 g sodium citrate dihydrate in 100 ml double-distilled water).

An egg yolk/citrate extender with 29.9 mM fucose was made up by making up egg yolk/citrate extender as described in the paragraph above and adding to it at 1:10 by volume 300 mM fucose in sterile double-distilled water.

A whole milk extender was made up by heating to 95° C. for 10 minutes, cooling and filtering and adding antibiotics thereto.

A whole milk extender with 27.9 mM fucose was made up by making up whole milk extender as described in the paragraph above and adding to it at 1:10 by volume 300 mM fucose in sterile double-distilled water.

For the experiment here, the frozen straws were thawed by immersing the straws in 37° C. water for one-half minute.

Seventy microliters from a thawed straw were mixed with 930 microliters of extender to provide semen extender admixture containing 2.6 million sperm per milliliter.

For each treatment, 40 microliters of semen extender admixture were added to 40 microliters of Sperm-TALP (described in Reference Example A hereinafter) containing 10 microliters of explant suspension (i.e., 10 μl concentrated explant suspension plus 30 μl Sperm-TALP). In each case, the total volume was 80 microliters. The 80 μl droplets were kept under silicone oil to prevent evaporation. The droplets were incubated for 10 minutes at 39° C. Then 20 μl samples were taken from the droplets and placed on microscope slides and videotaped, and the density of sperm on explants was determined in each case from the videotapes. The results in terms of density of sperm per 0.1 mm$^2$ of explant surface are set forth in Table 2 below:

TABLE 2

| Extender | Oviductal Isthmus | Oviductal Ampulla |
|---|---|---|
| 1) Egg yolk/citrate | 40.5 | 38.1 |
| 2) Egg yolk/citrate with 27.9 mM fucose | 7.0 | 12.6 |
| 3) Whole milk extender | 13.8 | 17.4 |
| 4) Whole milk extender with 27.9 mM fucose | 9.8 | 5.4 |

These experiments indicate effectiveness of fucose addition to extender in blocking binding of sperm to oviductal epithelium.

Reference Example A

Binding inhibition studies in respect to bovine sperm binding to oviductal epithelium were carried out as follows.

A modified Tyrode's balanced salt solution, termed Sperm-TALP was used as the medium for sperm and oviductal explants. The Sperm-TALP consisted of 99 mM NaCl, 3.1 mM KCl, 25 mM NaHCO$_3$, 0.35 mM NaH$_2$PO$_4$, 10 mM HEPES, 2 mM CaCl$_2$, 1.2 mM MgCl$_2$, 21.6 mM sodium lactate, 1.1 mg/ml sodium pyruvate, 6 mg/ml BSA (bovine serum albumin) and 1 μg/ml gentamycin, in water (pH 7.4, 290 mOsm/kg).

Semen was prepared as in Reference Example B.

Oviductal explants were prepared as follows: Oviducts associated with large follicles (>15 mm) were collected at an abattoir and transported on ice to the laboratory in sterile phosphate buffered saline (PBS) (pH 7.4) with penicillin (100 U/ml) and streptomycin (50 μg/ml). The PBS consisted of 136 mM NaCl, 2.68 mM KCl, 0.49 mM MgCl$_2$, 9.58 mM NaH$_2$PO$_4$, 1.47 mM KH$_2$PO$_4$ and 0.88 mM CaCl$_2$ in water. Upon arrival at the laboratory, the oviducts were thoroughly washed in PBS/penicillin/streptomycin, then dissected free of surrounding tissues. The isthmus was identified by its narrow width and thick muscular walls. It was separated from the remaining oviduct and straightened by cutting it free from mesentery. The oviductal epithelium was obtained as described in Lefebvre, R., et al, Biol. Reprod. 54, 575–582 (1996) by gently milking the isthmus with tweezers from the uterotubal junction towards the ampullary isthmic junction. Epithelium, which emerged in sheets, was collected in Sperm-TALP and disaggregated into small pieces by one passage through a 25-gauge needle attached to a 1-ml tuberculin syringe. Within 30 minutes of disaggregation, the clumps of epithelial cells formed everted vesicles with apical surfaces facing outward. These everted vesicles are referred to herein as explants. Explants were washed twice in Sperm-TALP by centrifugation (80 × g, 20 seconds), then allowed to settle in a dense layer at the bottom of a 30×10 mm petri dish.

Binding inhibition studies were carried out as follows: Aliquots (10 μl) were taken from the dense layer of explants and transferred to 50 μl droplets of Sperm-TALP under silicone oil. The droplets contained monosaccharides or oligosaccharides to be tested. The droplets of medium had been equilibrated under oil at 39° C. with humidified atmosphere. After 10 minutes, sperm were added to droplets, such that the droplet volume was 80 μl, the final sperm concentration was 1×10$^5$ motile sperm/ml and the final concentration of test substance was 30 mM for monosaccharides or 12.5 mM for oligosaccharides. After 15 minutes of co-incubation, the explants were washed free of loosely attached sperm by three transfers through 50 μl Sperm-TALP droplets. The explants were then transferred to slides and covered with coverslips supported by silicon grease for analysis of density of sperm binding.

In a first set of experiments, the monosaccharides fucose, mannose, sialic acid, glucose, N-acetyl glucosamine, and galactose were tested for binding inhibition.

In a second set of experiments, lacto-N-fucopyranose I (containing the linkage fucose α1–2 galactose), 3-fucosyllactose (containing the linkage fucose α1–3 glucose), Lewis-X which is α-L-fucose-[1–3]-[β-D-galactose-(1–4)]-D-N-acetylglucosamine (containing the linkage fucose α1–3 N-acetylglucosamine), and Lewis-a which is (α-L-fucose-[1–4]-[β-D-galactose-(1–3)]-D-N-acetylglucosamine) (containing the linkage fucose α1–4 N-acetylglucosamine) were tested for binding inhibition.

In a third set of experiments, the binding inhibition effect of acetylglucosamine 1-β-4[fucose 1-α-6] acetylglucosamine-O-Me (having the linkage fucose α1–6 N-acetylglucosamine) was compared to that of fucose and that of Lewis-a.

In the three sets of experiments, treatment effects on sperm binding per unit area of epithelium were analyzed by ANOVA using Systat. Post-hoc pairwise comparisons of means were made with the Tukey's HSD test. Three to five replicates were performed for each set of experiments. For each replicate, a different oviduct was incubated with frozen/thawed sperm from the same pool of three bulls.

In a fourth set of experiments, a dose-response curve was constructed for Lewis-a. A linear regression test was used to detect an effect of Lewis-a concentration on sperm binding density. The program was Systat (SPSS, Inc., Chicago, Ill.).

In the first set of experiments, only fucose significantly reduced sperm binding density compared to vehicle control.

In the second set of experiments, only Lewis-a produced significantly lower sperm binding density than the control.

In the third set of experiments, only fucose and Lewis-a produced significantly lower sperm binding density than the control.

In the fourth set of experiments, a significant dose response effect was observed for Lewis-a. The binding inhibition curve was shifted to the left of the curve produced by fucose (as described in Reference Example B) showing that Lewis-A provides a more potent effect than fucose. The results are depicted in the lower curve of FIG. 1.

Both fucose and Lewis-a were found not to cause agglutination of living sperm.

Reference Example B

Binding inhibition studies in respect to bovine sperm binding to oviductal epithelium were carried out as follows:

The Sperm-TALP solution described in Reference Example A was used as the medium for the experiments.

Semen was prepared as follows: Samples from three fertile Holstein bulls were diluted in milk extender, pooled, loaded into 0.5 ml artificial insemination straws at a concentration of $50 \times 10^6$ sperm per straw, frozen in liquid nitrogen vapor and held in liquid nitrogen tanks until used. For each treatment, two straws of frozen semen were thawed, diluted into 5 ml of Sperm-TALP solution, and centrifuged at 350 × g for 5 minutes. All but 1 ml of overlying medium was removed and the sperm were resuspended into the medium. The 1-ml sperm suspension was divided into four aliquots for selection of motile sperm by swim-up. Each 250 $\mu$l aliquot was layered under 1 ml of Sperm-TALP in a 15 ml centrifuge tube. After incubation for 1 hour at 39° C., 750 $\mu$l were removed from the top of each tube. Sperm were concentrated by centrifugation at 350 × g for 5 minutes and adjusted to $40 \times 10^6$ motile sperm/ml with Sperm-TALP. Motility ranged from 80–90%.

Explants of isthmic and ampullar epithelium were obtained from oviducts that had been surgically removed from preovulatory heifers.

Binding inhibition studies were carried out as follows: Aliquots (10 $\mu$l) taken from the dense layer of explants were added under silicone oil to 50 $\mu$l droplets of Sperm-TALP that contained as test compound either a glycoprotein or fucoidan, or a monosaccharide. The droplets of medium had been equilibrated under oil at 39° C. in a humidified atmosphere containing 5% $CO_2$. After 10 minutes, sperm were added to droplets, such that the final droplet volume was 80 $\mu$l, the final sperm concentration was $1.25 \times 10^6$ motile sperm/ml, and the final concentration of test substances was about 3 mg/ml for the glycoproteins and fucoidan, and 31 mM for the monosaccharides. After 15 minutes of co-incubation, the explants were washed free of loosely attached sperm by three transfers through 50 $\mu$l Sperm-TALP droplets and vigorous stirring. The explants were transferred to slides and covered with coverslips supported by silicon grease for analysis of sperm binding. Separate experiments were carried out on isthmic and ampullar epithelium.

The test compounds were fetuin, asialofetuin, ovalbumin, fucoidan, fucose, N-acetylglucosamine, and N-acetylglucosamine sulfate. Only oviductal explants treated with fucoidan (3 mg/ml; p<0.001, n=5) or fucose (31 mM, p<0.01, n=6) had reduced density of sperm compared to the controls. No significant differences were detected between isthmic and ampullar explants.

In testing, fucose did not cause agglutination of living sperm and fucoidan was found to cause agglutination of living sperm.

In another experiment, incubation of explants in increasing concentrations of fucose resulted in inhibition of sperm binding as depicted in the upper curve of FIG. 1.

Background Example 1

Oviductal epithelium was obtained as follows: Oviducts were collected at the time of slaughter (within 5 minutes of the heifer's death). Each oviduct was placed in a 500-ml Pyrex beaker containing 300 ml of phosphate buffered saline (PBS), pH 7.4, and transported on ice to the laboratory. Upon arrival, the oviductal epithelium was removed under aseptic conditions. Oviducts were thoroughly washed in PBS and then dissected free of the surrounding tissues and straightened as much as possible. A 1-cm piece of the duct at the ampullary-isthmic junction was removed and disposed of to ensure that the epithelium of that region was not included. The caudal isthmus (including the uterotubal junction) and the ampulla were kept separate. The ampullary segment was held at the infundibular region over a 15-ml conical tube containing 5 ml of SFRE-199-2 medium and gently squeezed along the outside towards the ampullary isthmic junction with a watchmaker's forceps. The isthmic region was held at the ampullary end, and the oviductal epithelium was pushed out through the uterotubal junction.

Uterine epithelium was collected by milking the tip of the uterine horn in similar fashion to that previously described for the oviduct.

The extruded tissues were allowed to settle for 5 min. The supernatant was then removed and discarded. After two washes in SFRE 199-2 medium (80 g, 30 sec), the epithelium was disaggregated into small pieces by one passage through a 25-gauge needle attached to a 1-ml tuberculin syringe. Within 30 min of disaggregation, the clumps of epithelial cells formed everted tubes with the apical surfaces of the epithelial cells on the external surface. These everted tubes are referred to as explants. The primary cultures of each region of the oviductal epithelium (isthmic and ampullary) were established by transferring 10 $\mu$l of the pellet of epithelial tissue into 350 $\mu$l of fresh SFRE 199-2 medium in a well of a 24-well plate. To maintain a high humidity in the test wells, the wells in each corner of the plate were filled with medium. The explants were incubated at 39° C. in a humidified atmosphere containing 5% $CO_2$. Viability of the explants was determined by looking for ciliary activity.

The same batch of frozen semen pooled from three fertile Holstein bulls and supplied by Select Sires (Plain City, Ohio) was used throughout the project. The semen had been diluted in an egg yolk citrate extender, loaded into 0.5 ml artificial insemination straws at a concentration of $50 \times 10^6$ motile sperm per straw, frozen in liquid nitrogen ($LN_2$) vapor, and held in $LN_2$ until used.

For each experiment, two straws of frozen semen were thawed by immersion in a water bath at 37° C. for 30 sec, diluted into 5 ml of Sperm-TALP solution (described in Reference Example A), and centrifuged at 350 × g for 5 min. All but 1 ml of the medium overlying the sperm pellet was removed, and the sperm were resuspended. Motile sperm were isolated by a swim-up procedure by layering 250 $\mu$l of the suspension under 1 ml of Sperm-TALP solution in each of four 15-ml centrifuge tubes. After incubation for 1 hour at 39° C., 750 $\mu$l was removed from the top of each tube. Sperm were concentrated by centrifugation at 350 × g for 5 min, and the numbers were adjusted to $40 \times 10^6$ motile sperm/ml.

The explants (10 $\mu$l of explants in 350 $\mu$l of SFRE-199-2 medium with 6 mg/ml bovine serum albumin medium) were inseminated with $10^7$ sperm per well, within 2 hours of tissue collection. Sperm were thoroughly distributed in the wells by gentle swirling, incubated with the explants 15 min, then swirled again before examination for binding.

The number of attached sperm was determined by reviewing videotapes, and tissue area was determined by using a digital-imaging and analysis system.

The experiment was replicated five times.

Figure 2:
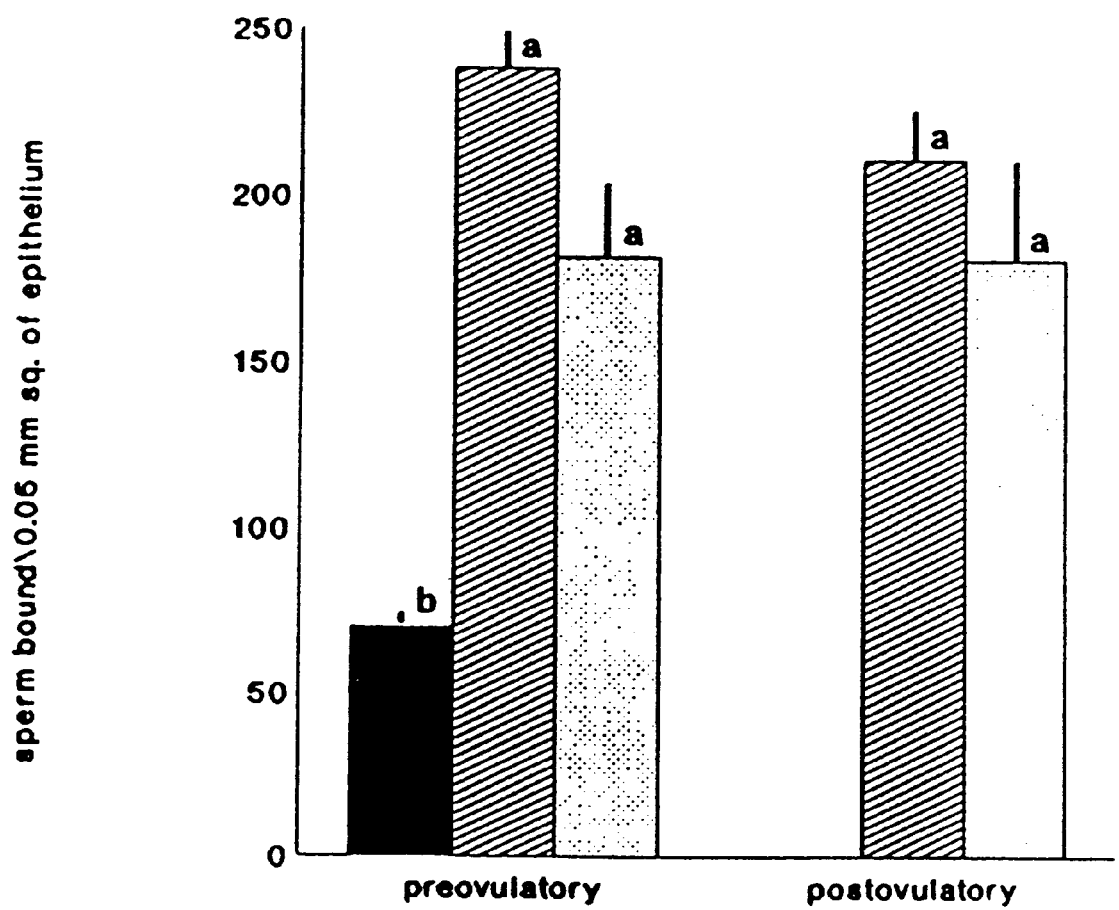
FIG. 2 depicts bar graph results of Background Example 1 showing sperm bound per 0.05 mm square of uterine and oviductal epithelium.

The results are depicted in FIG. 2 which shows mean±SEM sperm/0.05 mm² of epithelium for uterine epithelium (leftmost bar), oviductal isthmus epithelium (hatched bars) and oviductal ampullar epithelium (dotted bars). Different letters signify different numbers of sperm bound per unit area ($p<0.05$).

Background Example 2

Oviductal explants prepared as described in Reference Example B set forth above, were added to 50-µl droplets under oil containing α-L-fucosidase (0.1 U/mi₁ bovine epididymal fucosidase) for 5 hours at 39° C. in a humidified atmosphere containing 5% $CO_2$. Three controls were used to confirm the specific action of the fucosidase: (1) incubation of explants with fucosidase and its specific fucosidase inhibitor deoxyfuconojirimycin (dFJ, 2 mM); (2) incubation of explants with galactosidase; (3) incubation of explants with Sperm-TALP (described in Reference Example A) alone. Treated explants were transferred to a droplet of fresh Sperm-TALP and then sperm was added. The final volume was 80 µl, and the final sperm concentration was $1.25 \times 10^6$ motile sperm/ml. After 15 minutes of incubation, explants were washed and the sperm density was analyzed. The incubation with fucosidase caused a significant reduction in sperm binding compared to that in controls ($p<0.001$, $n=3$). No significant differences were detected among controls and between isthmic and ampullar explants. This experiment shows that binding of sperm to oviductal epithelium is due to fucose-containing molecule in the epithelium.

Because of the variations which will be obvious to those skilled in the art, the invention is defined by the claims.

What is claimed is:

1. Bull semen extender composition comprising fucose-containing bull sperm monovalent- binding compound in a reproduction efficiency increasing effective amount.

2. The bull semen extender composition of claim 1 which has an osmolality ranging from 280–320 mOsm.

3. The bull semen extender composition of claim 2 wherein said compound is present at a concentration ranging from 0.5 mm to 100 mM.

4. The bull semen extender composition of claim 2 wherein said compound is selected from the group consisting of fucose and oligosaccharide.

5. The bull semen extender composition of claim 4 wherein said compound is fucose present at a concentration of 7.5 mM to 75 mM.

6. The bull semen extender composition of claim 4 wherein said compound is oligosaccharide containing fucose in an α1–4 linkage to N-acetylglucosamine and is present in a concentration ranging from 1 mM to 20 mM.

7. The bull semen extender composition of claim 6 wherein said compound is Lewis-a.

8. The bull semen extender composition of claim 2 which also comprises cow's milk.

9. The bull semen extender composition of claim 2 which also comprises egg yolk.

10. Extended bull semen composition comprising bull semen in an amount providing a concentration of bull sperm ranging from $1 \times 10^6$ motile sperm/ml to $100 \times 10^6$ motile sperm/ml and bull semen extender composition, comprising fucose-containing, bull-sperm-monovalent-binding compound in a reproduction efficiency increasing effective amount and having an osmolality ranging from 280–320 mOsm.

11. The extended bull semen composition of claim 10 comprising a concentration of bull sperm less than $20 \times 10^6$ motile sperm per ml.

12. The extended bull semen composition of claim 10 comprising a concentration of bull sperm less than $10 \times 10^6$ motile sperm per ml.

13. The extended bull semen composition of claim 10 wherein the fucose-containing sperm monovalent binding compound is present at a concentration ranging from 0.5 mM to 100 mM based on the extender composition.

14. The extended bull semen composition of claim 10 wherein the fucose-containing sperm monovalent binding compound is selected from the group consisting of fucose and oligosaccharide.

15. The extended bull semen composition of claim 14 wherein the fucose-containing bull sperm monovalent binding compound is fucose present at a concentration of 7.5 mM to 75 mM based on the extender composition.

16. The extended bull semen composition of claim 14 wherein the fucose-containing bull sperm monovalent binding compound is oligosaccharide containing fucose in an α1–4 linkage to N-acetylglucosamine and is present at a concentration ranging from 1 mM to 20 mM based on the extender composition.

17. The extended bull semen composition of claim 16 wherein said oligosaccharide is Lewis-a.

18. The extended bull semen composition of claim 10 wherein the extender composition also comprises cow's milk.

19. The extended bull semen composition of claim 10 wherein the extender composition also comprises egg yolk.

20. A method of increasing the reproductive efficiency of bull semen for artificial insemination of cows comprising diluting it with the bull semen extender composition comprising fucose-containing bull sperm-monovalent binding compound in a reproductive efficiency increasing amount and having an osmolality ranging from 280–320 mOsm.

21. An extended bull semen composition where the reproductive efficiency of bull semen is increased for artificial insemination of cows, consisting essentially of a semen extender and a fucose-containing bull sperm monovalent-binding compound in a reproduction efficiency increasing amount, wherein the extender and fucose-containing bull sperm monovalent-binding compound has an osmolality ranging from 280–320 mOsm, and bull semen in an amount providing a concentration of bull sperm ranging from $1 \times 10^6$ to $100 \times 10^6$ motile sperm/ml.

* * * * *